United States Patent [19]

Schmidt et al.

[11] Patent Number: 4,639,243
[45] Date of Patent: Jan. 27, 1987

[54] PROCESS AND APPARATUS FOR OBTAINING BLOOD PLASMA

[76] Inventors: Baerbel Schmidt, Hirsch-Gereuth-Str. 27, D-8000 München 70; Walter Samtleben, Waldpromenade 102½, D-8035 Gauting, both of Fed. Rep. of Germany; Michael J. Lysaght, 33A Shoreline Rd., Barrington, Ill. 60010

[21] Appl. No.: 571,399

[22] Filed: Jan. 17, 1984

[30] Foreign Application Priority Data

Jan. 25, 1983 [DE] Fed. Rep. of Germany ....... 3302383

[51] Int. Cl.[4] .............................................. A61M 1/34
[52] U.S. Cl. ......................................... 604/6; 210/927
[58] Field of Search ....................................... 604/5, 6

[56] References Cited

U.S. PATENT DOCUMENTS

| 3,698,560 | 10/1972 | Tapp et al. | 210/321 |
| 3,705,100 | 12/1972 | Blatt et al. | 210/23 |
| 3,742,946 | 7/1973 | Grossman | 604/6 |
| 4,197,847 | 4/1980 | Djerassi | 128/214 R |
| 4,267,053 | 5/1981 | Hashino et al. | 210/650 |
| 4,284,502 | 8/1981 | Kramer | 604/6 |
| 4,381,775 | 5/1983 | Nose et al. | 604/6 |
| 4,409,106 | 10/1983 | Furuta et al. | 210/732 |
| 4,477,575 | 10/1984 | Vogel et al. | 436/170 |

FOREIGN PATENT DOCUMENTS

| A10001074 | 3/1979 | European Pat. Off. . |
| 0048901 | 4/1982 | European Pat. Off. . |
| 0070738 | 1/1983 | European Pat. Off. . |
| 7203008 | 5/1972 | Fed. Rep. of Germany . |
| 2939213 | 5/1980 | Fed. Rep. of Germany . |
| 597868 | 4/1978 | Switzerland . |
| 2055047 | 2/1981 | United Kingdom . |

OTHER PUBLICATIONS

Article entitled: Einfuhrung in die Physiologie des Menschen by Dr. Max Schneider—1964, p. 123.
Excerpt by C. L. J. Vink et al. from "Proceedings of the European Dialysis and Transpl. Association" (1965), pp. 265 and 266.

Primary Examiner—Brian E. Hearn
Assistant Examiner—O. Chaudhuri
Attorney, Agent, or Firm—Bradford R. L. Price

[57] ABSTRACT

A straight-forward, simplified process and apparatus for obtaining blood plasma are provided which employ no pumps or other external flow monitoring devices. Instead, a plasma filtering assembly is suspended a predetermined distance below the injection site to employ the forces of gravity to separate plasma from the other components of whole blood.

26 Claims, 2 Drawing Figures

PROCESS AND APPARATUS FOR OBTAINING BLOOD PLASMA

FIELD OF THE INVENTION

The invention relates primarily to the withdrawal of whole blood from humans and other warm-blooded animals for the purpose of collecting the blood plasma.

BACKGROUND AND OBJECTS OF THE INVENTION

Prior to this invention, in a process commonly referred to as donor plasmapheresis, about 500 ml of whole blood are collected from a human donor in a blood bag. The bag is centrifuged in a place spatially separate from the blood donor to separate the plasma from the other components of the whole blood (notably, red blood cells). After centrifugation, the plasma is removed and collected. After suspension in a sterile saline solution, the remaining components are returned to the donor.

Continuous and semicontinuous centrifuging systems for donor plasmapheresis also predate this invention. All of these systems require relatively expensive apparatus. In certain cases, these systems are also time-consuming.

Underlying the present invention is the problem of providing a straight-forward, simplified plasmapheresis process which can be carried out with an extremely low expenditure on apparatus.

In accordance with the present invention, the problem is solved by positioning only a plasma filtering unit between an injection cannula and the reservoirs for collecting the plasma filtrate and the other blood components.

The use of a plasma filter is, to be sure, known in principle in therapeutic plasmapheresis. Here, blood is taken continuously from the patient by puncture of a central venous vessel and pumped at a flow rate of 50 to 250 ml/min through a "separating system" which delivers a plasma filtrate flow of 10 to 80 ml/min. Simultaneously, the withdrawn plasma is replaced by means of a suitable albumin solution (for example, human albumin or deep-frozen plasma). The corresponding treatment takes 1 to 3 hours, during which about 1 to 5 liters of plasma are exchanged. Either a continuously operating centrifuge or a so-called membrane filter can be used as the "separating system" during therapeutic plasmapheresis. Such a membrane filter has a surface area of 1000 to 5000 $cm^2$. The membrane can be configured either as hollow fibers or as flat membranes. The membrane has a pore size which makes possible an unhampered passage of all the plasma proteins, but retains all the formed and cellular elements of the blood. Under certain geometrical and flow conditions, plasma free of cellular components and hemoglobin can be obtained.

However, such a plasma filtration process always requires blood pumps, various monitors, etc.

The use of membranes for donor plasmapheresis (for example, in U.S. Pat. Nos. 4,212,742 and 4,381,775) also always presupposes the use of relatively complicated apparatus, such as blood pumps. Furthermore, safety monitors and extensive special purpose materials (for example, tube systems with special pump segments, drop chambers with connecting pieces and transfer lines to the monitors, etc.) are used.

As a result, it can be stated that previous attempts to use a plasma filter are still more expensive than use of the above-mentioned centrifuging method.

SUMMARY OF THE INVENTION

In accordance with the invention, a process and apparatus for obtaining blood plasma are provided which employ no pumps or other external flow monitoring devices between the injection cannula and the collection reservoirs. Instead, the invention employs a plasma filtering unit as the sole separating device.

More particularly, the invention provides a plasmapheresis process during which a blood collection reservoir is suspended at a predetermined distance below a venous injection site. At the same time, external pressure is applied on the heart-side of the injection site. Whole blood is conveyed from the injection site to the blood collection reservoir through an intervening plasma filtering unit. Soley in response to the externally applied pressure and the force of gravity, the filtering unit separates the plasma from the whole blood. The plasma is collected in a collection reservoir which is suspended at or below the filtering unit.

Before the passage through the plasma filtering unit, an anticoagulant is preferably continuously added to the whole blood.

In a preferred embodiment, the blood collection reservoir is suspended about 35 to 100 cm below the injection site.

In one embodiment, the process of the invention also includes the step of returning the contents of the blood collection reservoir to the donor using the same plasma filtering unit, only now suspended in a changed gravitational position. In this changed gravitational position, the blood collecting reservoir is suspended a predetermined distance above the injection site.

In a preferred embodiment, in the changed gravitational position, the blood collection reservoir is suspended between about 30 cm and 280 cm above the injection site.

Since the process of the invention utilizes gravity and operates without blood pumps, drop chambers or other apparatus, with the exception of the plasma filtering unit itself, the invention provides a process which is not only usable with a minimum of apparatus, but which is extremely compact and makes do without the use of virtually any external energies.

The apparatus which embodies the features of the invention includes a single tube from an injection cannula to the plasma filtering unit and a tube to each of the collection reservoirs. The collection reservoir for blood plasma can, in the usual manner, be constructed as a transportable and storable bag or the like. The collection reservoir for blood, too, can be constructed as a bag for the blood to be stored or returned directly.

The plasma filtering unit may consist of hollow fibers or flat membranes aligned in flow direction. In accordance with one aspect of the invention, the hollow fibers have an inside diameter of 250 to 450 u, and preferably is 300 to 400 u. The blood film thickness between the flat membranes is between 250 and 450 u, and preferably is between 300 and 400 u.

The hollow fibers or flat membranes are used in a length from 5 to 30 cm, and preferably are 5 to 15 cm in length.

The apparatus which embodies the feature of the invention thus constitutes a compact unit which can be sold as a package.

DESCRIPTION OF THE PREFERRED EMBODIMENTS

Figure 1:
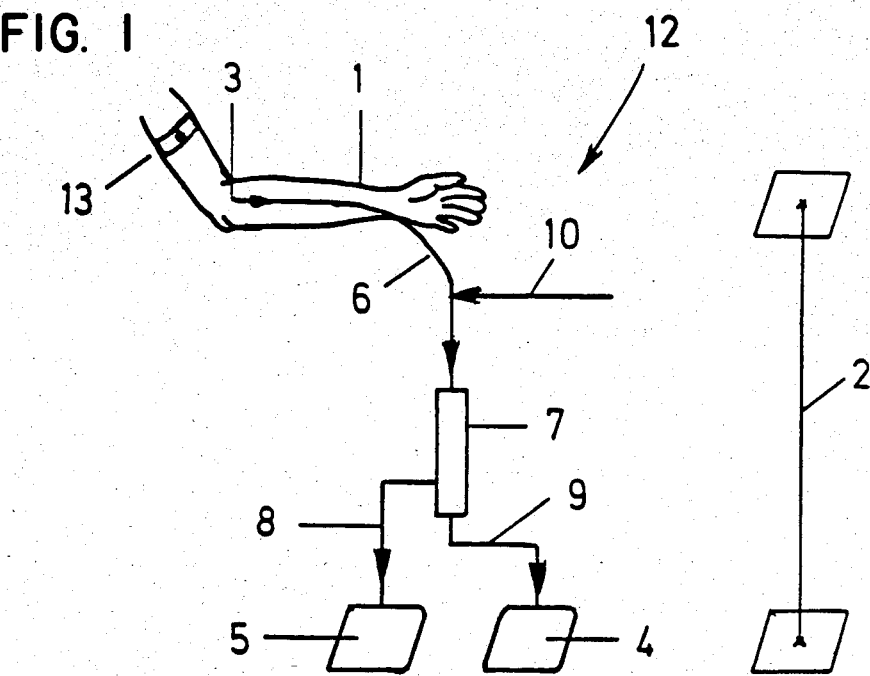
FIG. 1 is a diagrammatic view of a process and apparatus which embody the features of the invention and which are shown in the gravitational position used for separating and collecting blood plasma from whole blood.

A process and apparatus 12 for collecting blood plasma in accordance with the invention shown in FIG. 1.

The apparatus 12 which embodies the features of the invention includes an injection cannula 3 which is insertable into the vein in the arm 1 of a donor. The cannula 3 can be the kind usually used for blood collection procedures. The apparatus 12 further includes a plasma filtering unit 7 and a tube 6 which conveys whole blood withdrawn by the cannula 3 to the inlet of the filtering unit 7. A tube 10 conveys anticoagulant into the tube 6 upstream of the filtering unit 7.

The apparatus 12 also includes a plasma collection bag 5 and a tube 8 which conducts plasma from the filtering unit 7 to the bag 5.

The apparatus 12 further includes a red blood cell collection bag 4 and a tube 9 which conducts red blood cells from the outlet of the filtering unit 7 to the bag 4.

In use, during a plasmapheresis procedure, the process which embodies the features of the invention includes the step of placing a pressure sleeve 13 around the arm 1 of the donor on the heart-side of the injection site, i.e., between the shoulder and the elbow. The sleeve 13 is pumped up in a usual manner to create a pressure which is less than the diastolic pressure but greater than the normal venous pressure of the donor.

The process next includes the step of puncturing a large vein in the bend of the elbow with the cannula 3.

The process includes the step of suspending the blood collection bag 4 a predetermined distance (identified by numeral 2 in FIG. 1) below the injection site. Preferably, the distance 2 is about 35 to 100 cm below the injection site.

The plasma is collected in the plasma collection bag 5. The plasma collection bag 5 can be arranged at the height of or up to 30 cm below the filter 7. Lower positions are possible, depending upon the filter used. The subpressure arising, however, must not lead to hemolysis.

Here it is to be heeded that all the fitting pieces and connections 6, 8, and 9 used in the system 12 should have an inside diameter of at least 0.5 cm, in order to yield a hydraulic resistance which is as low as possible. If narrower parts should be needed in order to establish connections between various system sections, these narrower parts should be chosen to be as short in length as possible.

The filtering unit 7 consists of a microporous membrane. For the recovery of all the plasma protein components from the whole blood, the screen coefficient for the membrane should amount to approximately 1.0. In special cases, however, the membrane can be one which presents a permeability for only a few plasma proteins, for example for the recovery of albumin.

The filtering unit 7 should also present a special geometry.

If the membrane in the filtering unit 7 consist of hollow fibers, the inside diameter of the hollow fibers should lie between 250 to 450 u, and is preferably between 300 and 400 u. If membranes below these values or above these values are used, in the first case, the blood flow per time unit through the filtering unit 7 would be too low; and, in the second case, the ratio of the plasma filtration rate to the blood flow rate would be too low.

The hollow fiber length used can fluctuate between 5 and 30 cm. Lengths of 5 to 15 cm, however, are preferred, since a fiber extension beyond this range does not bring about an clear increase in the filtrate flow rate. The number of fibers in the filtering unit 7 can vary between 500 and 3000. With a given inside diameter and length of the hollow fibers, the filtrate flow rate increases linearly with the blood flow rate and the number of hollow fibers.

This means that the choice of the number of hollow fibers presents a compromise between the costs for the filter and the treatment duration.

Similar considerations also hold for a flat membrane filter. In this case, the blood layer thickness should vary between 250 and 450 u. Also the length should be between 5 and 30 cm, and is preferably between 5 and 15 cm. In order to meet these demands, the layer thickness and the number of layers with optimal filter operation must be adapted so that there results a total surface area of between 500 and 3000 $cm^2$. When layer thickness and length are chosen, there results a filtration rate proportional to the surface area. The choice of the surface area again represents a compromise between the costs for material and the treatment duration.

To prevent a coagulation of blood in the system 12 just presented, the filtering unit 7 is rinsed before use with an electrolyte solution with heparin or ACD added as an anticoagulant. Furthermore, the process includes the step of continuously introducing (via tube 10) a coagulation-inhibiting solution into the system 12 during the donation.

After approximately 500 ml of blood have been obtained from the donor, the blood constituent caught up in the blood collection bag 4 (notably red blood cells) can either be returned to the donor through the filtering unit 7 for the collection of additional blood plasma, or it can be returned directly to the donor bypassing the filter unit 7. The blood constituent in the bag 4 can also be retained and not returned to the donor, with or without additional filtration through the filtering unit 7.

If the blood constituent is to be given back to the donor, the pressure sleeve 13 is first removed from the arm 1. Then, in accordance with the invention, the blood collection container 4 is suspended in a changed gravitational position a predetermined distance (identified by numeral 11 in FIG. 2) above the injection site. Preferably the distance 11 is about 30 to 280 cm above the donor. If so desired, the rate of return of the blood constituent to the donor can be increased by means of an additional pressure (less than 200 mmHg) exerted on the blood collection bag 4.

The apparatus 12 can be commercially prefabricated and be placed on the market as a sterile packaged unit.

Two detailed examples are now described for the use of the process and apparatus of the invention:

EXAMPLE 1

The apparatus 12 usable for the process of the invention was assembled from the following parts:

(1) Injection cannula 3 (2.54 cm long; inside diameter 1.4 mm), obtained from the firm of Abbott, Article No. 4716;

(2) Tube system 6, 8, 9, and 10 obtained from the firm of Amicon, Article No. D-20SK (tube inside diameter 3/16 inches; all the fitting pieces wide-lumen);

(3) Plasma filtering unit 7 obtained from the firm of Travenol, being a Travenol CPS-10 plasma filter having an active hollow fiber length of approximately 21 cm; total length of 26 cm.; and 800 Plasmaphan hollow fibers (Enka) with an internal diameter of 320 to $330 \times 10^{16}$m; and (4) Collection bags 4 and 5: 500 ml. obtained from the firm of Fenwal, Article No. R 0817.

The parts were joined with one another in the sequence illustrated in FIG. 1. Anticoagulant solutions contained in the bags 4 and 5 was thrown out before use. During the plasma collection process as shown in FIG. 1, a continuous (2 ml/min) infusion of ACD solution BP, formula A, firm of Travenol (22.4 g/liter water-soluble dextrose BP, 22 g/liter sodium citrate, 8 g/liter citronic acid-monohydrate) was introduced (via tube 10) into the system 12 between injection site and the plasma filtering unit 7.

Before use, the filter 7 was rinsed with two liters of a saline solution that contained heparin (5000 IU/liter).

A donor was connected to the system 12 by way of puncture of an elbow curve vein of the arm 1, which was obstructed using the sleeve 13. The blood collection container 4 was arranged at a height of 2 to about 80 cm below the injection site 3.

After 14 minutes, 365 ml of blood were obtained in the blood collecting container 4 (approximately 25 ml/min) and 140 ml of plasma (approximately 10 ml/min) in the blood plasma container 5.

In the plasma collected using this process and the apparatus 12, it was not possible to measure any hemolysis spectral-photometrically. The albumin concentrations of the collected plasma were compared with the unfiltered output blood of the donor. There were no measurable concentration differences for albumin, IgM and B-liprotein before and after filtration. These protein analyses were carried out with a laser nephelometer.

In this first experiment the blood cell concentrate (contained in bag 4) was not given back to the donor.

EXAMPLE 2

The system 12 was assembled exactly as in Example 1, with the sole difference being that the filtering unit 7 was a Plasmaflux P2 plasma filter of the firm of Fresenius (active hollow fiber length approximately 20 cm; total module length approximately 25 cm; approximately 2400 Plasmaphan hollow fibers (Enka) having an inside diameter of $330 \times 10^{-6}$ m).

The filter 7 used in Examples 1 and 2 thus contained the same type of membrane, but the number of hollow fibers in the filter 7 of Example 2 was approximately three times as great.

Another blood donor (not the same one used in Example 1) was connected to the system 12 as described and shown in FIG. 1. The blood collecting container was placed 80 cm below the puncture place 3. After 8 minutes, 330 ml of red blood cells (approximately 40 ml/min) and 160 ml of plasma (approximately 20 ml/min) were collected.

The flow rates achieved in Example 2 were thus both higher than in Example 1 with a comparable filtrate fraction.

Figure 2:
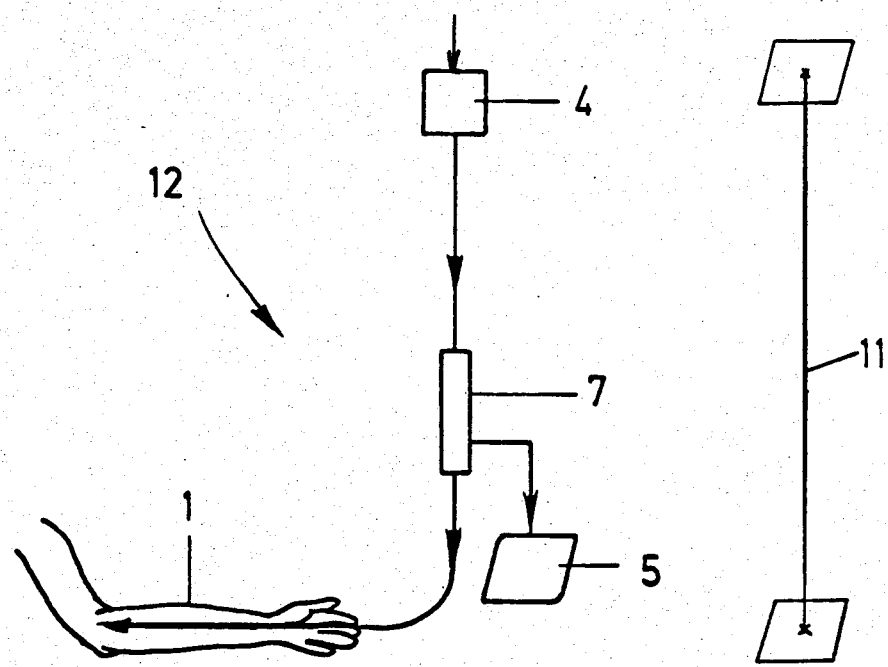
FIG. 2 is a diagrammatic view of the process and apparatus as generally shown in FIG. 1, but are now disposed in a changed gravitational position used for returning red blood cells to the donor.

The donor was then separated from the system 12. As shown in FIG. 2, the blood collecting bag 4 was arranged at a height 11 of about 180 cm over a reservoir, which during this experiment simulated the arm 1 of the donor. The blood concentrate recovered in the bag 4 during the first steps of the process was now conducted in a reverse direction through the filter 7 into the simulated arm 1. The blood flow rate was 165 ml/min; i.e., the entire content flowed back in approximately two minutes, and the plasma filtration rate was 33 ml/min. It was possible, therefore. to obtain 66 ml more of plasma in the plasma bag 5. As a result, it was possible to separate 235 ml of plasma in only 10 minutes.

The plasma was analyzed as in Example 1. No free hemoglobin was found there, and the plasma protein concentrations were identical with those of the unfiltered donor plasma.

We claim:

1. A process of collecting plasma from a donor comprising the steps of applying external pressure on the heart-side of a selected venous injection site on the donor, puncturing the injection site with a cannula, suspending a blood collection reservoir at a predetermined distance below the injection site so as to convey whole blood between the cannula and the blood collection reservoir through a plasma filtration unit to separate the plasma from the whole blood relying only upon the applied external pressure and the force of gravity, and collecting the separated plasma.

2. A process according to claim 1 wherein, during said step of suspending the blood collection reservoir, the blood collection reservoir is positioned at least about 35 cm below the injection site.

3. A process according to claim 1 wherein, during said step of suspending the blood collection reservoir, the blood collection reservoir is positioned between about 35 cm and 100 cm below the injection site.

4. A process according to claim 1 or 2 or 3 wherein, during said step of conveying whole blood through the plasma filtration unit, the whole blood is conveyed along a membrane having an effective length of between about 5 cm and 30 cm.

5. A process according to claim 4 wherein, during said whole blood conveying step, whole blood is conveyed along a membrane having a length of about 15 cm.

6. A process according to claim 1 or 2 or 3 wherein, during said step of conveying whole blood through the plasma filtration unit, the whole blood is conveyed along a membrane which defines a flow path having a thickness of between about $250\mu$ and $450\mu$.

7. A process according to claim 6 wherein, during said whole blood conveying step, whole blood is conveyed along a membrane which defines a flow path having a thickness of between about $300\mu$ and $400\mu$.

8. A process according to claim 1 or 2 or 3 wherein, during said step of conveying whole blood, the whole blood is conveyed through tubing which is attached to the inlet and outlet of the plasma filtration unit and which has an inside diameter of at least about 0.5 cm.

9. A process according to claim 1 or 2 or 3 and further including the steps, which follow said plasma collection step, of ceasing the application of externally applied pressure, suspending the blood collection reservoir a predetermined distance above the injection site, and returning the contents of the blood collection reservoir to the injection site through the plasma filtration unit.

10. A process according to claim 9 wherein, during said step of suspending the blood collection reservoir above the injection site, the blood collection reservoir is positioned at least about 30 cm above the injection site.

11. A process according to claim 10 wherein, during said step of suspending the blood collection reservoir above the injection site, the blood collection reservoir is positioned no more than about 280 cm above the injection site.

12. A process according to claim 9 and further including the step of collecting the additional plasma which is separated from the contents of the blood collection reservoir as the contents are returned through the plasma filtering unit to the injection site.

13. A process according to claim 1 or 2 or 3 wherein the external pressure application step includes the step of applying pressure which is less than normal diastolic pressure but greater than the normal venous pressure of the donor.

14. A process according to claim 1 or 2 or 3 wherein, during said step of collecting the separated plasma, a plasma collection reservoir is positioned at or below the height of the plasma filtration unit.

15. A process according to claim 14 wherein, during said step of collecting the separated plasma, the plasma collection reservoir is suspended not more than about 30 cm below the plasma filtration unit.

16. A process according to claim 1 or 2 or 3 and further including the step of introducing anticoagulant into the whole blood before it is conveyed through the plasma filtering unit.

17. An apparatus for collecting plasma from a donor comprising a cannula inserted in a venous injection site on the donor for withdrawing whole blood while an external pressure is applied on the heart-side of the injection site, a blood collection reservoir suspended a predetermined distance below said cannula, and, means for conveying whole blood between said cannula and said blood collection reservoir, said conveying means including filtration means positioned between said cannula and said reservoir for separating the plasma from the whole blood relying only upon the external pressure and the force of gravity, and means for collecting the separated plasma.

18. An apparatus according to claim 17 wherein said blood collection reservoir is suspended at least about 35 cm below said cannula.

19. An apparatus according to claim 17 wherein said blood collection reservoir is suspended between about 35 cm and 100 cm below said cannula.

20. An apparatus according to claim 17 wherein said filtration means includes a membrane having an effective length of between about 5 cm and 30 cm.

21. An apparatus according to claim 20 wherein said membrane has an effective length of about 15 cm.

22. An apparatus according to claim 20 wherein said membrane defines a flow path for the whole blood having a thickness of between about $250\mu$ and $450\mu$.

23. An apparatus according to claim 17 wherein said means for conveying whole blood includes conduit means attached to the inlet and outlet of said filtration means and having an inside diameter of at least about 0.5 cm.

24. An apparatus according to claim 17 wherein said plasma collection means is suspended at or below said plasma filtration means.

25. An apparatus according to claim 24 wherein said plasma collection means is suspended not more than 35 cm below said plasma filtration means.

26. An apparatus according to claim 17 and further including means for introducing anticoagulant into the whole blood before it is conveyed through said filtration means.

* * * * *